(12) United States Patent
Masuda et al.

(10) Patent No.: US 10,682,451 B2
(45) Date of Patent: Jun. 16, 2020

(54) CALIBRATION METHOD FOR FLOWMETERS IN BLOOD DIALYSIS SYSTEM

(71) Applicant: NIKKISO CO., LTD., Tokyo (JP)

(72) Inventors: Yoshimichi Masuda, Makinohara (JP); Masato Fujiwara, Makinohara (JP); Hiroshi Nimura, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 11 days.

(21) Appl. No.: 15/566,887

(22) PCT Filed: Apr. 11, 2016

(86) PCT No.: PCT/JP2016/061689
§ 371 (c)(1),
(2) Date: Oct. 16, 2017

(87) PCT Pub. No.: WO2016/171023
PCT Pub. Date: Oct. 27, 2016

(65) Prior Publication Data
US 2018/0133385 A1 May 17, 2018

(30) Foreign Application Priority Data
Apr. 22, 2015 (JP) .................. 2015-087476

(51) Int. Cl.
*A61M 1/16* (2006.01)
*A61M 1/36* (2006.01)
(Continued)

(52) U.S. Cl.
CPC ............ *A61M 1/1613* (2014.02); *A61M 1/16* (2013.01); *A61M 1/1656* (2013.01);
(Continued)

(58) Field of Classification Search
USPC ......................................................... 73/1.06
See application file for complete search history.

(56) References Cited

U.S. PATENT DOCUMENTS

| | | | | |
|---|---|---|---|---|
| 4,152,922 A | * | 5/1979 | Francisco, Jr. | ..... G01F 25/0007 73/1.21 |
| 5,111,683 A | * | 5/1992 | Fond | ........................ A61M 1/16 702/100 |

(Continued)

FOREIGN PATENT DOCUMENTS

| CN | 104248781 A | 12/2014 |
|---|---|---|
| JP | S60-152916 A | 8/1985 |

(Continued)

OTHER PUBLICATIONS

Jun. 28, 2016 International Search Report issued in International Patent Application No. PCT/JP2016/061689.

(Continued)

*Primary Examiner* — Peter J Macchiarolo
*Assistant Examiner* — Mohammed E Keramet-Amircolai
(74) *Attorney, Agent, or Firm* — Oliff PLC

(57) ABSTRACT

Provided is a calibration method for flowmeters in a blood dialysis system, whereby highly accurate calibration can be performed even by omitting a reference flowmeter not directly relating to dialysis therapy. This calibration method comprises: while preventing outflow into a blood channel in a blood purifier, supplying a liquid to a channel, said channel passing through an inflow flowmeter and an outflow flowmeter; and then calibrating the inflow flowmeter and the outflow flowmeter correction whereby, at the time of liquid supply, a value measured by the outflow flowmeter is equalized to a value measured by inflow flowmeter.

16 Claims, 13 Drawing Sheets

(51) Int. Cl.
*A61M 1/26* (2006.01)
*G01F 25/00* (2006.01)

(52) U.S. Cl.
CPC .......... *A61M 1/267* (2014.02); *A61M 1/3643* (2013.01); *A61M 1/3663* (2013.01); *G01F 25/0007* (2013.01); *A61M 1/166* (2014.02); *A61M 1/3627* (2013.01); *A61M 2205/3334* (2013.01); *A61M 2205/3368* (2013.01); *A61M 2205/3389* (2013.01); *A61M 2205/70* (2013.01)

(56) References Cited

U.S. PATENT DOCUMENTS

| | | | | |
|---|---|---|---|---|
| 5,170,656 | A * | 12/1992 | Draus | G01F 25/0007 73/1.22 |
| 6,697,742 | B1 * | 2/2004 | Franklin | G01D 18/00 702/100 |
| 2006/0016243 | A1 * | 1/2006 | Nevius | G01F 1/66 73/1.16 |
| 2008/0108930 | A1 * | 5/2008 | Weitzel | A61B 5/02152 604/5.04 |
| 2016/0320227 | A1 * | 11/2016 | Cunningham | G01F 25/0007 |

FOREIGN PATENT DOCUMENTS

| | | | |
|---|---|---|---|
| JP | S 60152916 | * 8/1985 | ............... G01F 1/00 |
| JP | S63-111422 A | 5/1988 | |
| JP | H01-131669 A | 5/1989 | |
| JP | H09-239024 A | 9/1997 | |

OTHER PUBLICATIONS

Aug. 28, 2019 Office Action issued in Chinese Patent Application No. 201680023285.8.

Nov. 12, 2019 Office Action issued in Japanese Patent Application No. 2017-514074.

* cited by examiner

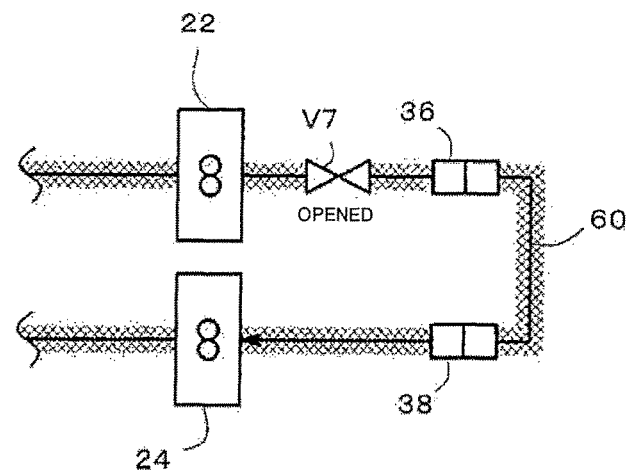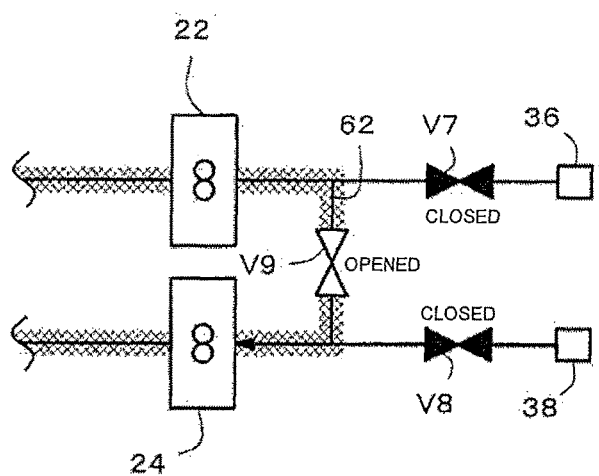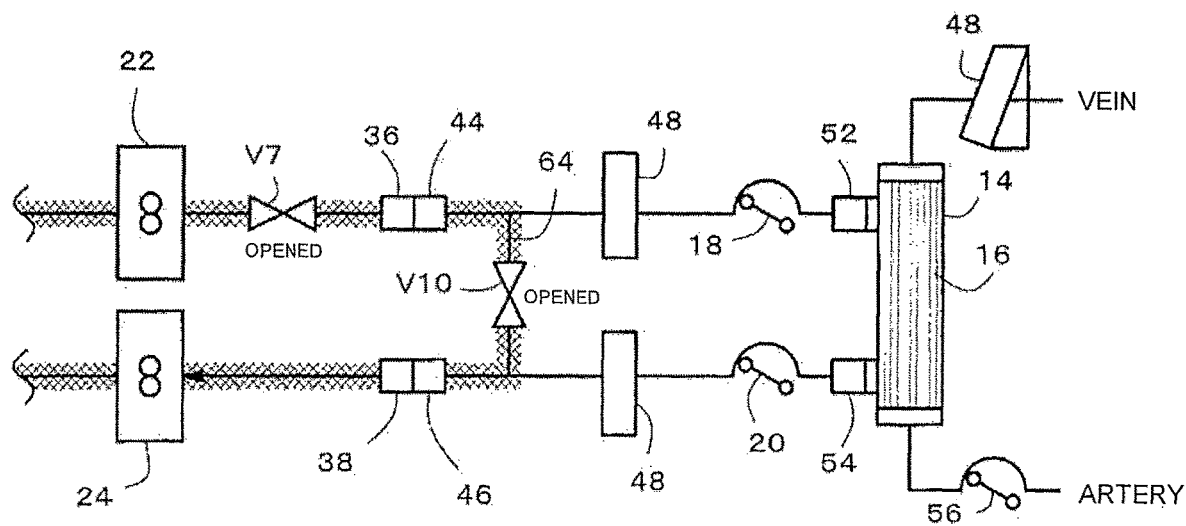
FIG. 9

CALIBRATION METHOD FOR FLOWMETERS IN BLOOD DIALYSIS SYSTEM

TECHNICAL FIELD

The present invention relates to a calibration method for a plurality of flowmeters disposed in a blood dialysis system.

BACKGROUND

Blood purifiers called dialyzers are used for dialysis therapy. A dialyzer includes a casing that houses a bundle of hollow fiber membranes. The casing includes four ports: a blood inflow port for introducing blood extracted from a shunt forming in a dialysis patient, for example, a blood outflow port for reinfusing blood into the patient, and dialysate inflow/outflow ports for inflow and outflow of the dialysate.

For dialysis therapy, blood is extracted out of the body (blood extraction) and conveyed to the dialyzer. Blood flows into the dialyzer via the blood inflow port, flows through hollow fiber membranes and out from the outflow port, and is returned to the body (reinfusion of blood). In addition, dialysate is supplied into the casing via the dialysate inflow/outflow port to fill between the hollow fiber membranes. The blood and dialysate undergo substance exchange via the hollow fiber membranes.

Further, in order to substitute for the function of the kidney to adjust the water content, the dialyzer is used to perform fluid removal for discharging excessive water content out of the body in the dialysis therapy. In the fluid removal process, the quantity of flow of dialysate is controlled to increase the quantity of outflow of dialysate compared to the quantity of inflow of dialysate, so that negative pressure is generated within the casing to thereby extract the water content within the blood toward the dialysate (i.e., by ultrafiltration).

Because an excessive quantity of fluid removal applies a load on the dialysis patient, it is necessary to measure the quantity of fluid removal accurately. Patent Document 1 describes obtaining a difference between measurements by a flowmeter disposed in the dialysate inflow channel and measurements by a flowmeter disposed in the dialysate outflow channel to thereby calculate the quantity of fluid removal.

In general, the allowable range of error in fluid removal is extremely limited, and positive displacement flowmeters such as oval flowmeters and Roots type flowmeters are used for such a requirement for high accuracy. The positive displacement flowmeter is configured to transfer liquid via a measurement chamber. Because the volume of the measurement chamber is known, the quantity of flow can be measured with high accuracy.

While the positive displacement flowmeters provide highly accurate measurement, it is technically difficult to cause the positive displacement flowmeter disposed close to the dialysate inflow channel and the positive displacement flowmeter disposed close to the dialysate outflow channel to output completely identical measurements, because each measurement value contains a measurement error based on the individual difference. It is therefore necessary to perform calibration in order to eliminate the measurement error between these two flowmeters. More specifically, a reference flowmeter capable of measuring the volume of liquid which is actually supplied accurately (at least to a degree which satisfies the required accuracy) is used to correct each of the measurements of the two flowmeters.

CITATION LIST

Patent Literature

PATENT DOCUMENT 1: JP H01-131669 A

SUMMARY

Technical Problem

There is an increasing need for cost reduction of whole blood dialysis systems, and elimination of a member not directly affecting the dialysis therapy has been studied. It is therefore an object of the present invention to provide a calibration method for flowmeters in a blood dialysis system, capable of achieving highly accurate calibration even when a reference flowmeter not directly affecting dialysis therapy is eliminated.

Solution to Problem

The present invention relates to a calibration method for flowmeters in a blood dialysis system. The blood dialysis system includes a blood purifier including a dialysis membrane, to which dialysate and blood are supplied to undergo substance exchange therebetween, via the dialysis membrane, a liquid feeding pump configured to supply the dialysate to the blood purifier, a liquid discharging pump configured to discharge the dialysate from the blood purifier, an inflow flowmeter configured to measure a quantity of flow of the dialysate to be supplied to the blood purifier, an outflow flowmeter configured to measure a quantity of flow of the dialysate to be discharged from the blood purifier, and a computing unit configured to measure a quantity of fluid removal from the blood based on a difference in measurements between the inflow flowmeter and the outflow flowmeter. With this calibration method, liquid is supplied to a flow channel passing through the inflow flowmeter and the outflow flowmeter while outflow of the liquid to a blood flow channel in the blood purifier is being prevented, and correction is performed to match the measurements of the outflow flowmeter obtained when the liquid is supplied with the measurements of the inflow flowmeter, thereby calibrating the inflow flowmeter and the outflow flowmeter.

In preferred embodiments of the invention, the calibration may be performed when a bypass route that bypasses the liquid feeding pump and the liquid discharging pump is formed.

In another example calibration method for flowmeters in a blood dialysis system, the blood dialysis system includes a blood purifier comprising a dialysis membrane, to which dialysate and blood are supplied to undergo substance exchange therebetween via the dialysis membrane, a liquid feeding pump configured to supply the dialysate to the blood purifier, a liquid discharging pump configured to discharge the dialysate from the blood purifier, an inflow flowmeter configured to measure a quantity of flow of the dialysate to be supplied to the blood purifier, an outflow flowmeter configured to measure a quantity of flow of the dialysate to be discharged from the blood purifier, and a computing unit configured to measure a quantity of fluid removal from the blood based on a difference in measurements between the inflow flowmeter and the outflow flowmeter. With this calibration method, an entire quantity of liquid having a known volume is supplied to a flow channel passing through the inflow flowmeter and the outflow flowmeter while outflow of the liquid to a blood flow channel in the blood purifier is being prevented, and the measurements of the inflow flowmeter and the outflow flowmeter are calibrated based on the known volume.

In preferred embodiments of the invention, the liquid having a known volume may be obtained by filling a tank having a known volume with the liquid to an upper limit of the volume.

In preferred embodiments of the invention, the liquid having a known volume may be obtained by storing the liquid in a tank including a liquid level sensor and acquiring measurements of the liquid level sensor.

In preferred embodiments of the invention, the liquid having a known volume may be obtained by storing the liquid in a container including a weight sensor and acquiring measurements of the weight sensor.

In preferred embodiments of the invention, the inflow flowmeter and the outflow flowmeter may be calibrated during a last rinsing process in a washing process of supplying washing liquid to the flow channel passing through the inflow flowmeter and the outflow flowmeter and rinsing the washing liquid.

Advantageous Effects of Invention

The present invention enables highly accurate calibration of flowmeters in a blood dialysis system even when a reference flowmeter is eliminated. This structure can reduce the size of the blood dialysis system and reduce the manufacturing costs.

BRIEF DESCRIPTION OF DRAWINGS

FIG. 9 explains an example bypass route according to the present embodiment.

DESCRIPTION OF EMBODIMENTS

Overall Structure

Figure 1:
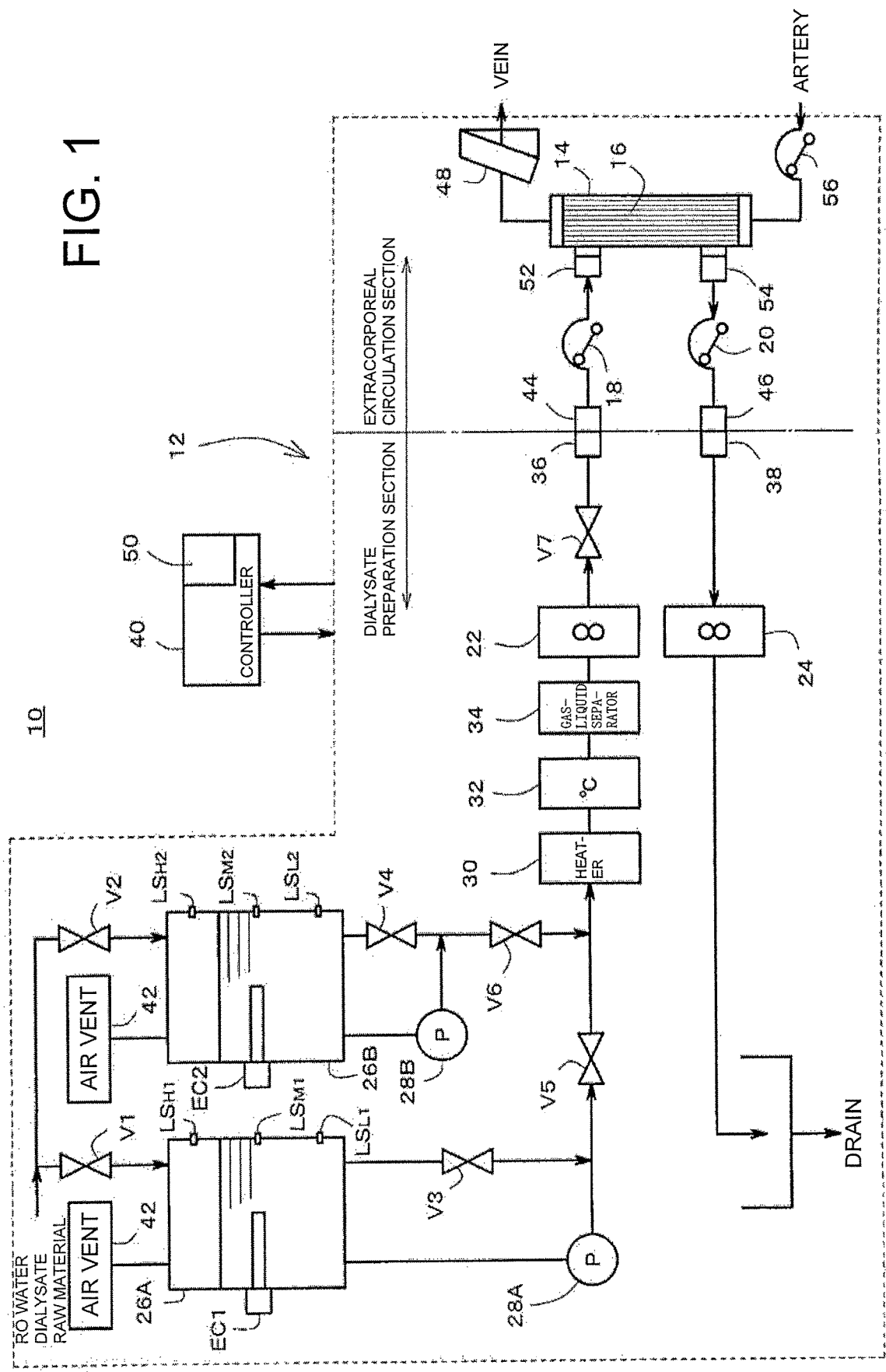
FIG. 1 schematically illustrates a blood dialysis system according to the present embodiment.

FIG. 1 schematically illustrates a blood dialysis system 10 according to an embodiment of the invention. The blood dialysis system 10 includes a blood dialyzer 12 and a blood purifier 14. In terms of function, the blood dialysis system 10 is divided into a dialysate preparation section and an extracorporeal circulation section, as illustrated in FIG. 1.

Dialysate produced in the dialysate preparation section is delivered to the extracorporeal circulation section. In the extracorporeal circulation section, the dialysate is supplied to the blood purifier 14. Blood is also supplied to the blood purifier 14 through another flow channel. A dialysate flow channel and a blood flow channel are separated from each other via a hollow fiber membrane 16 serving as a dialysis membrane. Substance exchange between the dialysate and the blood is performed via this hollow fiber membrane 16.

By increasing the amount of liquid to be discharged by a liquid discharging pump 20 disposed in the extracorporeal circulation section so as to be greater than the amount of liquid to be supplied by a liquid feeding pump 18 also disposed in the extracorporeal circulation section, a negative pressure is caused within the blood purifier 14, so that the water content within the blood is extracted into the dialysate via the hollow fiber membrane 16 (removal of fluid).

The quantity of fluid removal is obtained based on a difference in the measurements between the inflow flowmeter 22 and the outflow flowmeter 24 disposed in the dialysate preparation section. As will be described below, in the present embodiment, during calibration, correction is performed to match the measurement of the outflow flowmeter 24 with the measurement of the inflow flowmeter 22, to thereby calibrate the inflow flowmeter 22 and the outflow flowmeter 24.

Details of Each Element

The blood dialyzer 12 includes various consumable members installed in the extracorporeal circulation section. The consumable members include a purifier-side In coupler 44, a purifier-side Out coupler 46, a dialysate In coupler 52, a dialysate Out coupler 54, a coupler-coupler flow channel member (tube), the blood purifier 14, the artery side flow channel member (tube) of the extracorporeal circulation section, a vein side flow channel member (tube), and a clamp 48.

The purifier-side In coupler 44 can be coupled with a device-side In coupler 36 disposed at the inlet end of the blood dialyzer 12. The purifier-side Out coupler 46 can be coupled with a device-side Out coupler 38 disposed at the outflow end of the blood dialyzer 12. The purifier-side In coupler 44 and the purifier-side Out coupler 46 can be coupled with each other.

The dialysate In coupler 52 is coupled with a dialysate inflow port of the blood purifier 14. When the liquid feeding pump 18 is a tube pump, a tube (flow channel member) between the purifier-side In coupler 44 and the dialysate In coupler 52 forms a part of the tube pump and is squeezed by a roller.

Similarly, the dialysate Out coupler 54 is coupled with a dialysate outflow port of the blood purifier 14. When the liquid discharging pump 20 is a tube pump, a tube (flow channel member) between the purifier-side Out coupler 46 and the dialysate Out coupler 54 forms a part of the tube pump and is squeezed by a roller.

The blood purifier 14 is also called a dialyzer, and includes a bundle of hollow fiber membranes 16 and a casing for storing the bundle of hollow fiber membranes 16. The casing includes a total of four ports: a blood inflow port for introducing blood drawn from a shunt, for example, which is produced for a dialysis patient; a blood outflow port for reinfusing blood to the patient; and the dialysate inflow/outflow ports for inflow and outflow of the dialysate.

The blood flowing through the blood inflow port is returned into the body from the blood outflow port via the hollow fiber membrane 16. The dialysate flowing from the dialysate inflow port fills the external space of the hollow fiber membrane 16. The blood and the dialysate undergo substance exchange through the hollow fiber membrane 16 (dialysis membrane).

The clamp 48 is used to stop inflow and outflow of blood to and from the blood purifier 14, as will be described below. During calibration for the flowmeters described below, the clamp 48 stops inflow of the liquid into the blood circuit via the hollow fiber membrane 16.

Details of Each Element in Blood Dialyzer

The blood dialyzer 12 produces dialysate and controls the quantity of flow of the dialysate. For fluid removal, the blood dialyzer 12 calculates the quantity of fluid removal. The blood dialyzer 12 includes, from the upstream thereof, a first tank 26A, a second tank 26B, stirring pumps 28A and 28B, a heater 30, a temperature sensor 32, a gas-liquid separator 34, an inflow flowmeter 22, the device-side In coupler 36, the liquid feeding pump 18, the liquid discharging pump 20, the device-side Out coupler 38, an outflow flowmeter 24, and a controller 40.

Both the first tank 26A and the second tank 26B prepare and store the dialysate. The first tank 26A and the second tank 26B are formed of a sealed tank, for example, and include an air vent 42 for communicating between the interior of the tank and the atmosphere. The air vent 42 has a function of letting the air within the tank out of the tank when storing liquid in the tank and blocking foreign materials from entering the tank.

Both the first tank 26A and the second tank 26B are connected toward upstream of the flow channel passing through the inflow flowmeter 22 and the outflow flowmeter 24. To enable gravity feed, the first and second tanks 26A and 26B are preferably disposed relatively upward in the normal direction in the overall structure of the blood dialyzer 12.

Each of the first and second tanks 26A and 26B includes a liquid level sensor for measuring the volume (liquid level) of the dialysate. More specifically, concerning the first tank 26A, the volume (liquid level) of the dialysate within the first tank 26A is measured by three level sensors: a low water level sensor $LS_{L1}$ for detecting the volume in the relatively low water level region; a high water level sensor $LS_{H1}$ for detecting the volume in the relatively high water level region; and an intermediate water level sensor $LS_{M1}$, for detecting the volume in the region between the above two regions. Similarly, the second tank 26B includes a low water level sensor $LS_{L2}$, a high water level sensor $LS_{H2}$, and an intermediate water level sensor $LS_{M2}$. Various liquid level sensors including float level sensors, ultrasonic level sensors, capacitance type level sensors, optical level sensors, and other level sensors, may be used for the level sensors $LS_{L1}$, $LS_{M1}$, $LS_{H1}$, $LS_{L2}$, $LS_{M2}$, and $LS_{H2}$.

As described above, according to the present embodiment, measurements of the level sensors that measure the volume of the dialysate within the first and second tanks 26A and 26B can be used to obtain the volume of liquid which flows down to the inflow flowmeter 22 and the outflow flowmeter 24. As will be described below, it is possible to calibrate the inflow flowmeter 22 and the outflow flowmeter 24 by allowing an entire quantity of liquid having a known volume to flow down to the inflow flowmeter 22 and the outflow flowmeter 24 and comparing the measurements (integrated quantity of flow [L]) of the inflow flowmeter 22 and the outflow flowmeter 24 with the known volume of liquid [L].

The first and second tanks 26A and 26B may further include concentration sensors EC1 and EC2 for measuring the concentration of the dialysate. The concentration sensors EC1 and EC2 are formed of electric conductivity meters (EC meters), for example.

The stirring pumps 28A and 28B are driven when preparing the dialysate (mixing a raw material with pure water) in the first and second tanks 26A and 26B. As will be described below, concerning the first tank 26A, the stirring pump 28A is driven with the valve V3 being opened and the valve V5 being closed. Concerning the second tank 26B, the stirring pump 28B is driven with the valve V4 being opened and the valve V6 being closed.

The stirring pumps 28A and 28B may also be driven to supply the dialysate to the blood purifier 14 during priming or dialysis therapy, in addition to during preparation of the dialysate.

The heater 30 is used to heat the dialysate to temperatures close to the body temperature of the patient. The dialysate which is heated is measured by the temperature sensor 32, and the temperature setting of the heater 30 is feedback controlled based on the measurements. The gas-liquid separator 34 removes dissolved oxygen in the dialysate and gas in the liquid to prevent air bubbles from flowing into the blood purifier 14 located downstream.

The liquid feeding pump 18 feeds the dialysate stored in the first and second tanks 26A and 26B to the blood purifier 14. The liquid feeding pump 18 is disposed in the flow channel between the purifier-side In coupler 44 and the blood purifier 14. The liquid feeding pump 18 may be formed of a tube pump.

Tube pumps, which belong to known technology, will be described only briefly. By pressing an elastic tube such as a silicon tube externally with a roller to squash the tube, and then squeezing the tube in this state with the roller, liquid inside the tube moves in the squeezing direction. The liquid within the tube is transferred by continuously squeezing the tube in this manner. The structure of a tube pump in which only a tube comes in contact with the dialysate results in an advantage that the tube pump can be used hygienically simply by changing the tube.

The liquid discharging pump 20 is provided to discharge (draw) the dialysate from the blood purifier 14. The liquid discharging pump 20 is disposed in the flow channel between the blood purifier 14 and the purifier-side Out coupler 46. The liquid discharging pump 20, similar to the liquid feeding pump 18, may be formed of a tube pump.

The liquid feeding pump 18 and the liquid discharging pump 20 may be formed of a pump other than a tube pump. Pumps that do not block the flow channel, such as a centrifugal pump, may be used, for example.

The inflow flowmeter 22 measures the quantity of flow of dialysate to be supplied to (to flow into) the blood purifier 14. The inflow flowmeter 22 further measures the quantity of flow of washing liquid when the washing liquid, in place of dialysate, is passed through the flow channel of the blood dialyzer 12. The inflow flowmeter 22 is formed of a positive displacement flowmeter such as an oval flowmeter and a Roots type flowmeter, for example.

Positive displacement flowmeters, which belong to known technology, will be described only briefly. A positive displacement flowmeter includes a pair of rotors and a casing which houses the pair of rotors. A measuring chamber is formed between the rotors and an inner wall surface of the casing. When fluid enters the casing, the rotors are revolved. At this time, with the revolution of the rotors, the fluid flows downstream via the measuring chamber. One revolution of the rotors feeds the fluid corresponding to the volume of the measuring chamber (e.g., 0.25 mL) downstream. The number of revolutions of the rotor is output as a pulse signal, for example, and the number of revolutions is counted to obtain the integrated quantity of flow.

The outflow flowmeter 24 measures the quantity of flow of dialysate to be discharged (caused to flow out) from the blood purifier 14. The outflow flowmeter 24 also measures the quantity of flow of washing liquid when the washing liquid, in place of the dialysate, is passed through the flow channel of the blood dialyzer 12. The outflow flowmeter 24, similar to the inflow flowmeter 22, is formed of a positive displacement flowmeter, for example.

The device-side In coupler 36, which is disposed at the end portion of the blood dialyzer 12 on the inflow side, is coupled with the purifier-side In coupler 44 so that the device-side In coupler 36 and the purifier-side In coupler 44 are fluidly connected with each other. The device-side Out coupler 38, which is disposed at the end of the blood dialyzer 12 on the outflow side, is coupled with the purifier-side Out coupler 46, so that the device-side Out coupler 38 and the purifier-side Out coupler 46 are fluidly connected with each other. The device-side In coupler 36 and the device-side Out coupler 38 can be coupled with each other.

As will be described below, during priming and dialysis therapy, the device-side In coupler 36 and the purifier-side In coupler 44 are coupled with each other, and the device-side Out coupler 38 and the purifier-side Out coupler 46 are coupled with each other. During the preparation stage and washing, the device-side In coupler 36 and the device-side Out coupler 38 are coupled with each other and the device-side In coupler 44 and the purifier-side Out coupler 46 are coupled with each other.

The blood dialyzer 12 includes a plurality of valves. Specifically, the blood dialyzer 12 includes a valve V1 disposed in a flow channel between a supply source (not shown) of the pure water and the raw materials and the first tank 26A, and a valve V2 disposed in a flow channel between the supply source and the second tank 26B. The blood dialyzer 12 further includes a valve V5 disposed in a flow channel connecting a flow channel between the stirring pump 28A and the heater 30 and a valve V3 disposed in a flow channel connecting a flow channel between the stirring pump 28A and the valve V5 with the first tank 26A.

The blood dialyzer 12 further includes valves V4 and V6 disposed in a flow channel connecting the flow channel between the valve V5 and the heater 30 with the second tank 26B. A flow channel from the stirring pump 28B is connected to a flow channel between the valves V4 and V6.

The blood dialyzer 12 further includes a valve V7 in a flow channel between the inflow flowmeter 22 and the device-side In coupler 36. These valves V1 to V7 can be preferably controlled to be opened and closed by the controller 40, and are formed of solenoid valves, for example.

The controller 40 may be formed of a computer, for example, including a CPU, a storage unit, and a device/sensor interface, which are not shown, connected with each other via an internal bus. The storage unit of the controller 40 stores programs for executing calibration for the flowmeters, for example.

The controller 40 controls various operations of the elements forming the blood dialyzer 12 via the device/sensor interface. Specifically, the controller 40 controls opening and closing operations of the valves V1 to V7. The controller 40 further controls driving of the stirring pumps 28A and 28B. In addition, the controller 40 controls the temperature setting of the heater 30 based on the measurements of the temperature sensor 32. The controller 40 further controls driving of the liquid feeding pump 18 and the liquid discharging pump 20 based on the quantity of flow measurements from the inflow flowmeter 22 and the outflow flowmeter 24.

The controller 40 receives signals from various sensors via the device/sensor interface. The controller 40 receives measurements of the liquid volume (liquid quantity) of the first tank 26A from the level sensors $LS_{L1}$, $LS_{M1}$, and $LS_{H1}$. The controller 40 also receives measurements of the liquid volume (liquid quantity) of the second tank 26B from the level sensors $LS_{L2}$, $LS_{M2}$, and $LS_{H2}$.

The controller 40 further receives measurements of the liquid concentration in the first tank 26A from the concentration sensor EC1. Similarly, the controller 40 receives measurements of the liquid concentration in the second tank 26B from the concentration sensor EC2.

The controller 40 further receives measurements of the temperature of the liquid passing through the heater 30 from the temperature sensor 32. The controller 40 further receives, from the inflow flowmeter 22, measurements of the liquid quantity of flow supplied from at least one of the first and second tanks 26A and 26B. Similarly, the controller 40 receives, from the outflow flowmeter 24, measurements of the liquid quantity of flow flowing out from the blood purifier 14.

The measurements of the liquid quantity of flow may be received in the form of integrated quantity of flow values from the flowmeters or pulse signals in accordance with revolution of the rotors in the flowmeters. When the inflow flowmeter 22 and the outflow flowmeter 24 have a computing function, for example, the controller 40 receives the integrated quantity of flow values from these flowmeters. When these flowmeters do not have a computing function, the controller 40 receives pulse signals from the inflow flowmeter 22 and the outflow flowmeter 24, and, based on the pulse count, calculates the integrated quantity of flow values in a computing unit 50.

The controller 40 includes the computing unit 50. The computing unit 50 obtains a difference in the measurements between the inflow flowmeter 22 and the outflow flowmeter 24, and, based on this difference, calculates the quantity of fluid removal from blood in the dialysis therapy.

Dialysis Therapy Process

Figure 2:
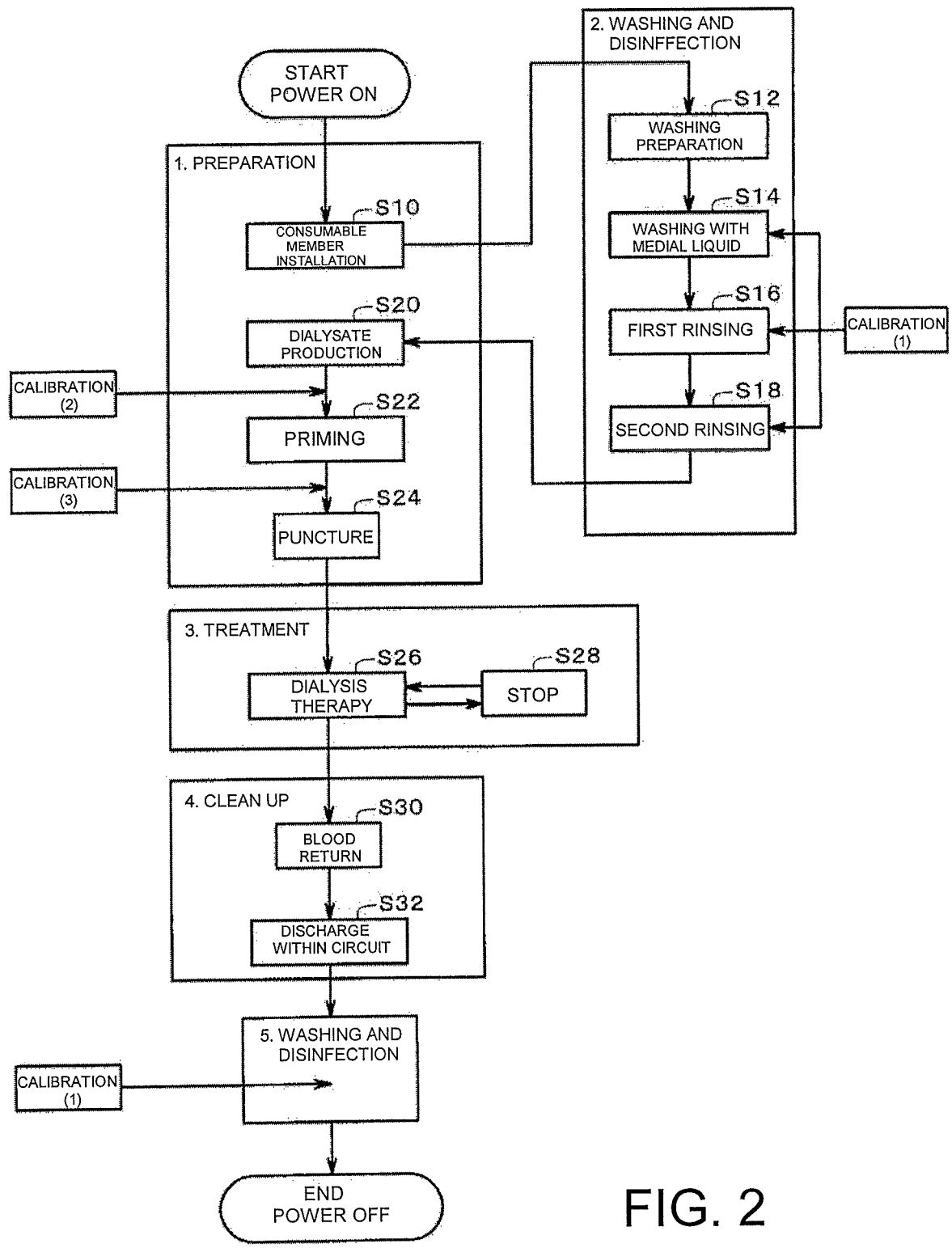
FIG. 2 illustrates flow of blood dialysis according to the present embodiment.

FIG. 2 illustrates a flowchart of a dialysis therapy process in the blood dialysis system according to the present embodiment. The flowchart of the dialysis therapy process includes the following five processes: preparation (1), washing and disinfection (2), treatment (3), cleaning-up (4), and washing and disinfection (5). Each process will be described in detail below.

First, in the preparation process (1), a user of the blood dialyzer 12 turns the power source of the apparatus on, and installs consumable members (S10). In this step, the consumable members are installed so as to prevent washing liquid from flowing into the blood circuit in the extracorporeal circulation section. The device-side In coupler 36 and the device-side Out coupler 38 are coupled with each other.

The process then proceeds to the washing and disinfection process (2) and preparation for washing is performed (S12). Specifically, washing liquid (medical fluid) is allowed to be stored in the first tank 26A and the second tank 26B. The volume of the washing liquid in the first tank 26A is measured by the level sensors $LS_{L1}$, $LS_{M1}$, and $LS_{H1}$, and the volume of the washing liquid in the second tank 26B is measured by the level sensors $LS_{L2}$, $LS_{M2}$, and $LS_{H2}$.

Figure 3:
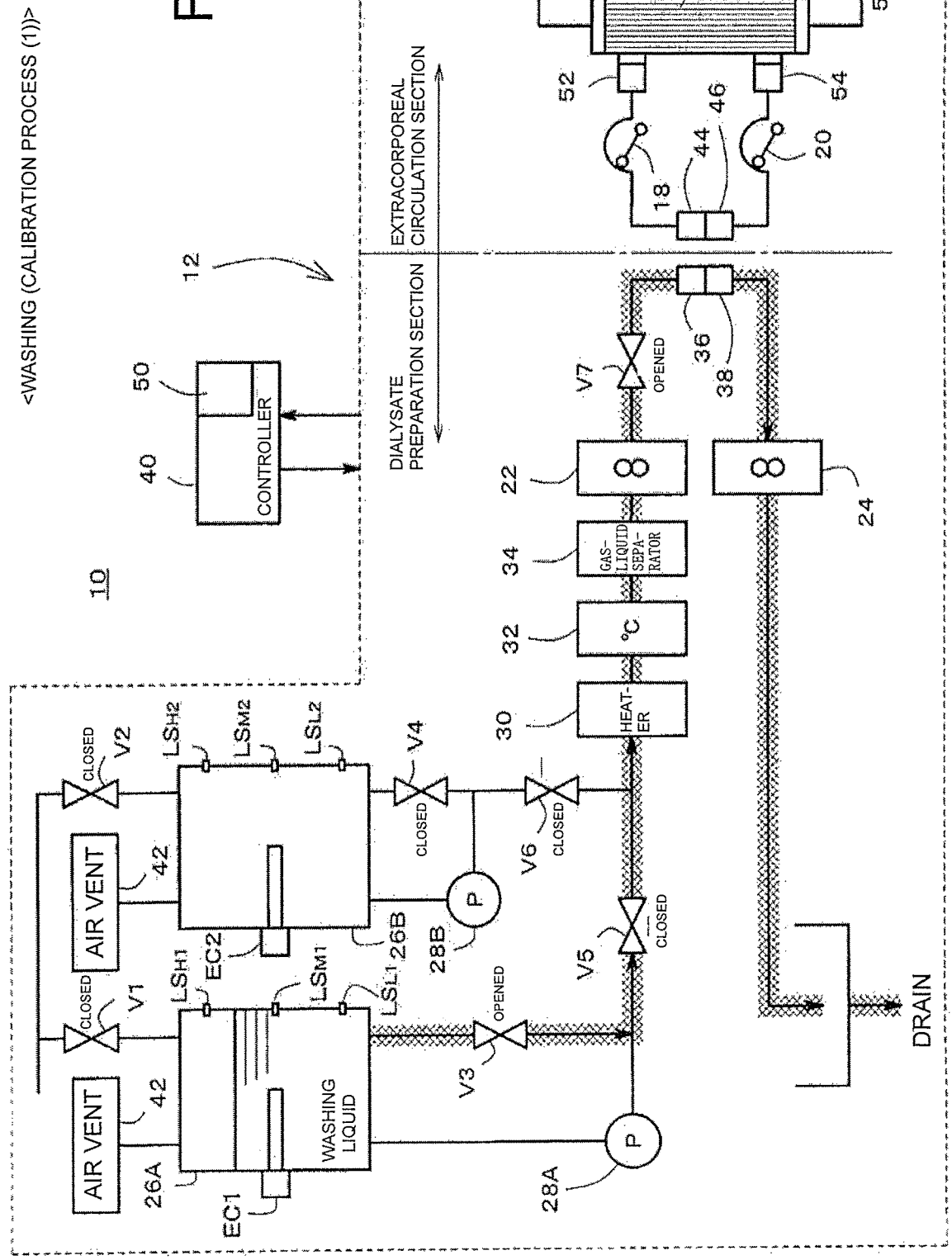
FIG. 3 explains a washing process and a calibration process (1) according to the present embodiment.

Then, the washing liquid is passed through the liquid flow channels in the blood dialyzer 12 (S14). When the washing liquid stored in the first tank 26A is used, the valves V3, V5, and V7 are opened and the remaining valves are closed, as illustrated in FIG. 3. At this time, the washing liquid falls by gravity by means of the water head pressure of the first tank 26A. Alternatively, the stirring pump 28A may be driven to supply the washing liquid.

When supplying the washing liquid through gravity feed, the flow route through which the washing liquid flows is as follows, as indicated by cross-hatching in FIG. 3: first tank 26A→valve V3→valve V5→heater 30→temperature sensor 32→gas-liquid separator 34→inflow flowmeter 22→valve V7-→device-side In coupler 36→device-side Out coupler 38→outflow flowmeter 24→drain.

While FIG. 3 illustrates an example in which the washing liquid in the first tank 26A is used for washing, the washing liquid in the second tank 26B may be used for washing. In this case, the valves V3 and V5 are closed and the valves V4 and V6 are opened. The opening and closing of the remaining valves and the flow path of the washing liquid are the same as those in the example described above.

After all of the washing liquid stored in the first tank 26A or the second tank 26B is passed, the flow channel which has been washed is rinsed with water (S16). Specifically, pure water is supplied to at least one of the first tank 26A and the second tank 26B, and is passed through the flow channel through which the washing liquid has been passed. This rinsing with pure water may be performed a plurality of times, such as twice (S18).

Figure 4:
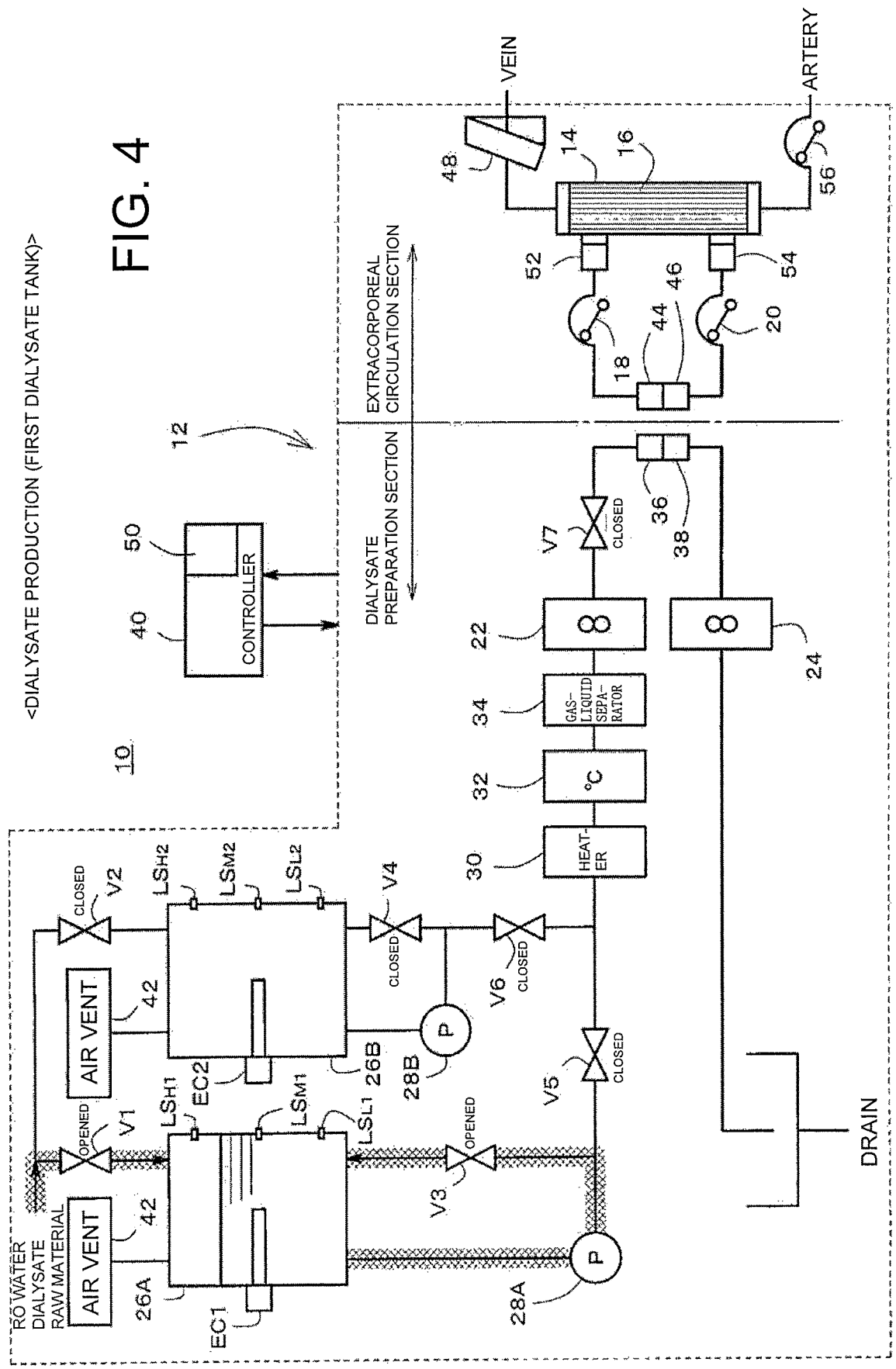
FIG. 4 explains a dialysate production process.

The process then returns to the preparation process (1), and the dialysate is produced (S20). At this time, as illustrated in FIG. 4, the valves V1 and V3 are opened, while the remaining valves are closed. Pure water and a raw material are supplied from a supply source to the first tank 26A. Driving the stirring pump 28A forms a circulating flow channel as indicated by cross-hatching in FIG. 4, and the pure water and the raw material are stirred together. The volume of the dialysate which is prepared (produced) is measured by the level sensors $LS_{L1}$, $LS_{M1}$, and $LS_{H1}$.

Figure 5:
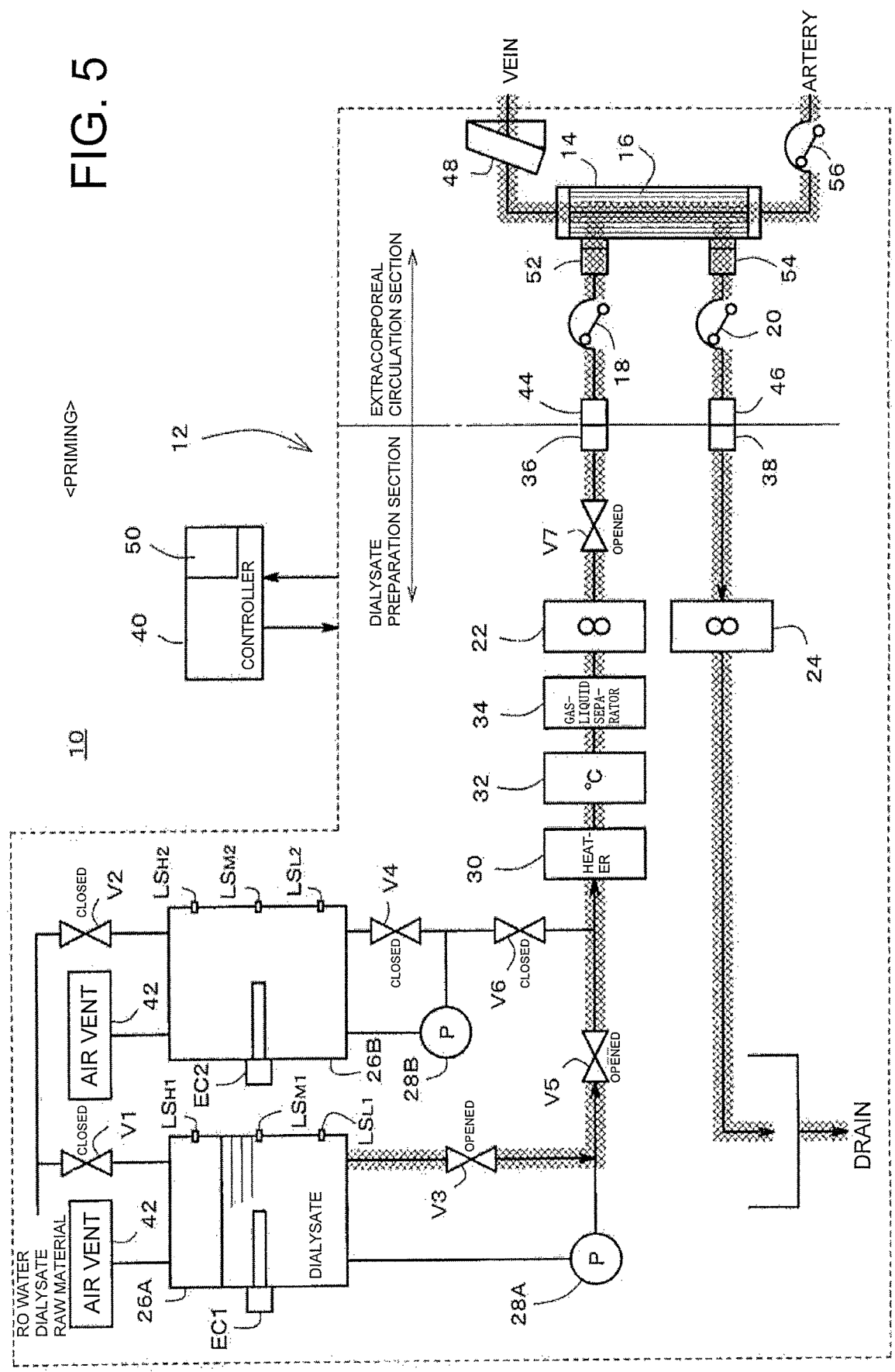
FIG. 5 explains a priming process.

Priming is then performed (S22). Priming is performed for ventilation and washing of the blood circuit and the blood purifier 14. As illustrated in FIG. 5, during priming, the valves V3, V5, and V7 are opened while the remaining valves are closed. Also, the device-side In coupler 36 and the purifier-side In coupler 44 are coupled with each other and the device-side Out coupler 38 and the purifier-side Out coupler 46 are coupled with each other. In this state, the liquid feeding pump 18, the liquid discharging pump 20, the blood pump 56, and the clamp 48 are caused to operate to fill the blood purifier 14 and the blood circuit with the dialysate. At this time, the heater 30 may be actuated to heat the blood purifier 14 and the blood circuit to temperatures close to the body temperature of a patient.

After priming, a needle for blood drawing and a needle for blood reinfusion are inserted into a shunt created for a patient who is subjected to the dialysis therapy (S24).

Figure 6:
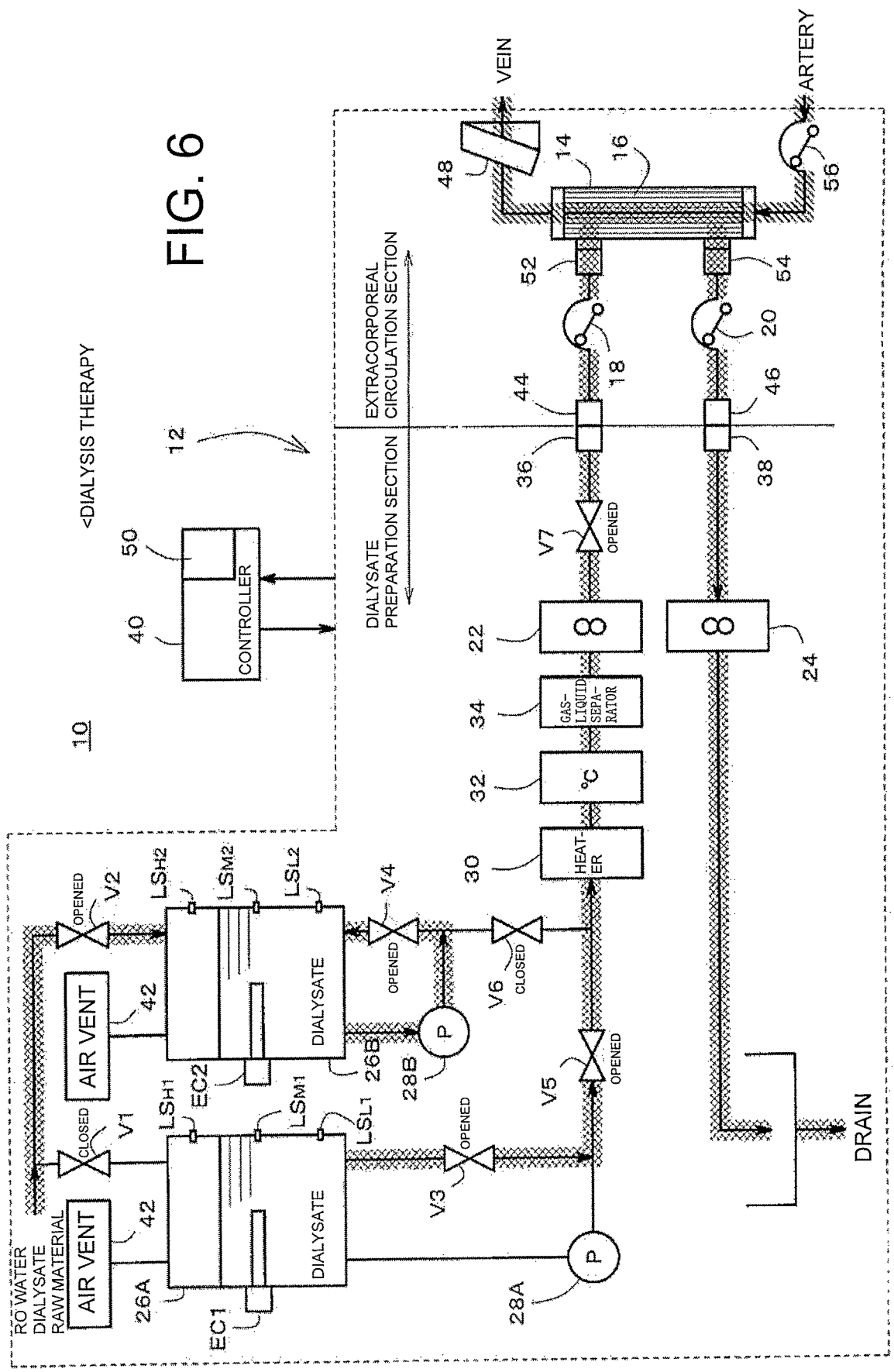
FIG. 6 explains a dialysis therapy process.

The treatment process (3) is then performed. As indicated by cross-hatching in FIG. 6, the dialysate is delivered to the blood purifier 14. Further, as indicated by slanting line hatching, blood is also delivered to the blood purifier 14. While, in the example illustrated in FIG. 6, the dialysate is supplied from the first tank 26A, via the valve V3, to the blood purifier 14, the dialysate may be supplied using the pump 28A, with the valve V3 being closed. In this case, during priming (FIG. 5) which is the previous stage of the treatment process, the dialysate is also supplied using the pump 28A with the valve V3 being closed. During the treatment process, the dialysate and the blood undergo substance exchange through the hollow fiber membrane 16 serving as the dialysis membrane (S26). Consequently, molecular weight substances in the blood such as urea nitrogen and creatinine, and electrolytes such as sodium and potassium are at least partially removed from the blood.

At this time, in order to perform fluid removal, the quantity of liquid to be discharged from the liquid discharging pump 20 is increased to be greater than the quantity of liquid to be supplied by the liquid feeding pump 18. The quantities of flow from the respective pumps are measured by the inflow flowmeter 22 and the outflow flowmeter 24, respectively, and the difference between them is obtained by the computing unit 50. The controller 40 controls the quantity of liquid supplied by the liquid feeding pump 18 and the quantity of liquid discharged by the liquid discharging pump 20 in accordance with the quantity of fluid removal based on this difference.

At this time, the dialysate for the next operation may be produced (prepared) in the second tank 26B by opening the valve V4 and driving the stirring pump 28B.

When a warning is generated, for example, during the dialysis therapy, the treatment is paused as a safety measure (S28).

After a prescribed quantity of dialysate is supplied, the process proceeds to the cleaning-up process (4). The blood within the blood circuit is first returned to the patient (S30), and the dialysate within the flow channel in the blood dialyzer 12 is discharged (S32).

The process further proceeds to the washing and disinfection process (5). During this process, the operation similar to that in the washing process (2) is performed. Upon completion of the washing and disinfection process (5), the blood dialyzer 12 is powered off to terminate the dialysis therapy process.

Calibration for Flowmeters

In the blood dialysis system according to the present embodiment, the inflow flowmeter 22 and the outflow flowmeter 24 are calibrated. For the calibration, with outflow of liquid to the blood channel (blood circuit) being prevented in the blood purifier 14, liquid is supplied to a flow channel including the inflow flowmeter 22 and the outflow flowmeter 24 and each of the flowmeters is caused to measure the quantity of flow. Regarding these measurements (integrated quantities of flow), the measurements from the outflow flowmeter 24 are corrected to match the measurements from the inflow flowmeter 22. In other words, the calibration according to the present embodiment uses the inflow flowmeter 22 as a reference flowmeter.

The dialysate containing a solute such as protein in the blood flows through the outflow flowmeter 24. This solute may adhere to gears of the rotors of the outflow flowmeter 24, or, even if such adhered matter is removed through washing, deterioration may proceed due to the adhered matter. For these reasons, the outflow flowmeter 24 tends to suffer from a greater error in measurement than that of the inflow flowmeter 22. According to the present embodiment, measurements of the outflow flowmeter 24 are calibrated using the inflow flowmeter 22 as a reference.

Flowmeter Calibration Process (1)

Timing for actually executing calibration will be described below. First, according to a first embodiment of the calibration process, calibration is executed during the washing and disinfection process (2) or the washing and disinfection process (5), as indicated in FIG. 2.

More specifically, calibration is performed in the step of passing the washing liquid through the flow channel of the blood dialyzer 12 (S14) and the step of rinsing with water (S16 and S18) during the washing and disinfection process (2) or the washing and disinfection process (5). Calibration is preferably performed in the final rinsing step (S18) in which the least quantity of residues such as protein exists within the flow channel, among the indicated steps. FIG. 3 illustrates, by hatching, the flow channel formed in step S18 in which the final rinsing step during the washing process is performed.

As indicated, the flow channel through which the washing liquid flows forms a bypass route which bypasses the liquid feeding pump 18 and the liquid discharging pump 20. As described above, when the liquid feeding pump 18 and the liquid discharging pump 20 are formed of tube pumps, a tube, which is a flow channel member, is squashed by the roller of the tube pump and blocked. Therefore, to allow the washing liquid to flow through, it is necessary to drive the liquid feeding pump 18 and the liquid discharging pump 20.

At this time, a difference between the quantity of liquid to be supplied and the quantity of liquid to be discharged, which is caused based on the individual difference between the liquid feeding pump 18 and the liquid discharging pump 20, would lead to a difference in the quantity of flow between the inflow flowmeter 22 and the outflow flowmeter 24. Further, with the movement of the liquid feeding pump 18 and the liquid discharging pump 20, pulsation is caused in the flow of liquid, which leads to fluctuation in the quantity of flow.

As the calibration of the inflow flowmeter 22 and the outflow flowmeter 24 is based on the precondition that the quantities of flow of the liquid flowing through the two flowmeters are equal, such a difference between the quantity of liquid to be supplied and the quantity of liquid to be discharged would mean this precondition is not met, making highly accurate calibration difficult to perform. It is also difficult to obtain accurate quantity of flow measurements under the environment in which the quantity of flow fluctuates.

Therefore, in the calibration process (1), calibration is performed while a bypass route which bypasses the liquid feeding pump 18 and the liquid discharging pump 20 is formed, thereby avoiding fluctuation in the quantity of flow by these pumps. Further, because, in addition to the liquid feeding pump 18 and the liquid discharging pump 20, other pumps including the stirring pumps 28A and 28B, for example, are not driven when the washing liquid is supplied by gravity feed, as described above, generation of pulsation can be avoided.

When the washing liquid is supplied using the stirring pumps 28A and 28B, calibration preferably starts upon elapse of a predetermined time after start of the pumps, because pulsation of the pumps is relatively large at the time of starting. When the pulsation is sufficiently small, the liquid may be supplied from the first tank 26A using the stirring pump 28A with the valve V3 being closed.

Calibration Process (2) According to Present Embodiment

According to another example calibration process, calibration may be performed between the dialysate producing step (S20) and priming (S22), as indicated in FIG. 2.

Figure 7:
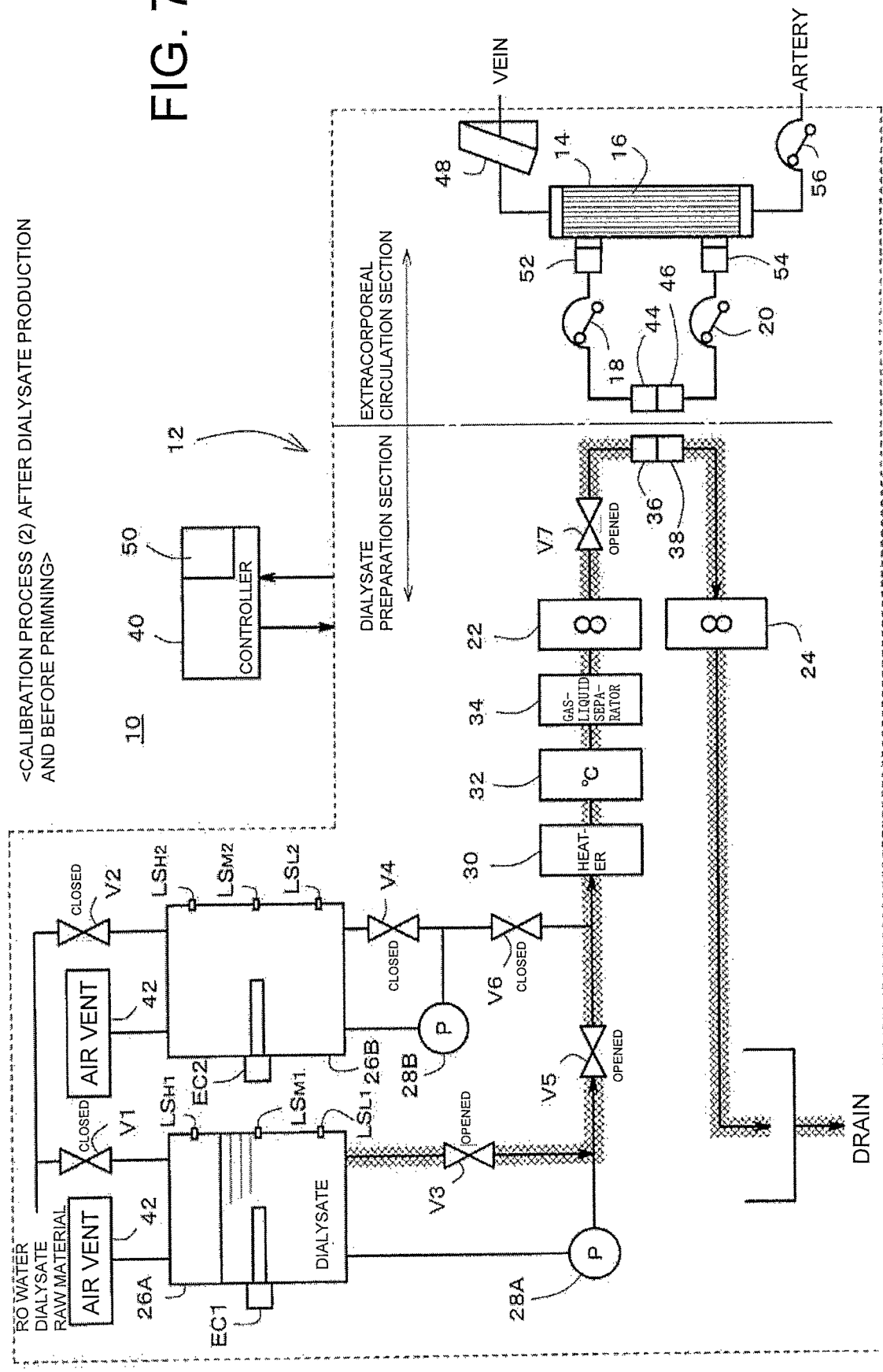
FIG. 7 explains a calibration process (2) according to the present embodiment.

FIG. 7 illustrates an example calibration process (2). Prior to execution of priming, the device-side In coupler 36 and the device-side Out coupler 38 are coupled with each other, and a bypass route which bypasses the liquid feeding pump 18 and the liquid discharging pump 20 is formed. Further, the dialysate is used as liquid flowing in the flow channel. For supplying the dialysate, gravity feed may be adopted in a manner similar to that in the calibration process (1).

As such, in the calibration process (2), similar to the calibration process (1), calibration can be performed using a flow channel which bypasses the liquid feeding pump 18 and the liquid discharging pump 20. Also, use of the liquid which is actually used in the dialysis therapy enables more accurate calibration than that in the calibration process (1).

In this calibration process (2) and the calibration process (3) which will be described below, an entire quantity of the dialysate whose volume is measured by the level sensors $LS_{L1}$, $LS_{M1}$, and $LS_{H1}$ (or the level sensors $LS_{L2}$, $LS_{M2}$, and $LS_{H2}$) may be supplied to the flow channel including the inflow flowmeter 22 and the outflow flowmeter 24. In this case, correction is performed to match the measurements of the inflow flowmeter 22 and the outflow flowmeter 24 with the measurements by the level sensors $LS_{L1}$, $LS_{M1}$, and $LS_{H1}$ (or the level sensors $LS_{L2}$, $LS_{M2}$, and $LS_{H2}$). At this time, the integrated quantity of flow [L], in place of the flow rate [mL/min], is used as the measurements of the inflow flowmeter 22 and the outflow flowmeter 24. The calibration to match the integrated quantity of flow [L] based on the measurements of the inflow flowmeter 22 and the outflow flowmeter 24 with the volume [L] of the dialysate measured by the level sensors enables calibration of the absolute values of the measurements of the inflow flowmeter 22 and the outflow flowmeter 24.

Calibration Process (3) According to Present Embodiment

According to another example calibration process, calibration may be executed between priming (S22) and puncture (S24), as indicated in FIG. 2.

Figure 8:
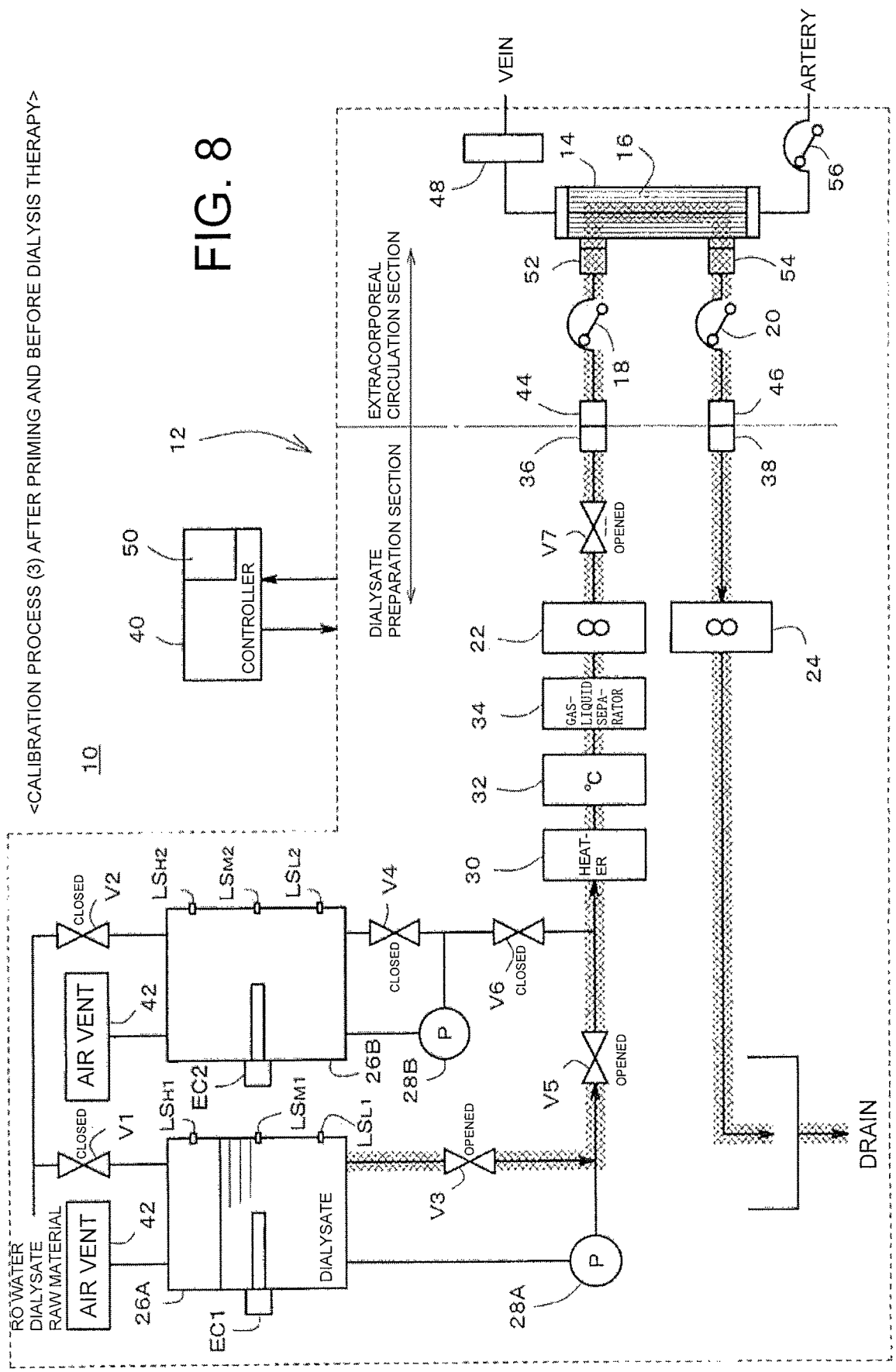
FIG. 8 explains a calibration process (3) according to the present embodiment.
Figure 10:
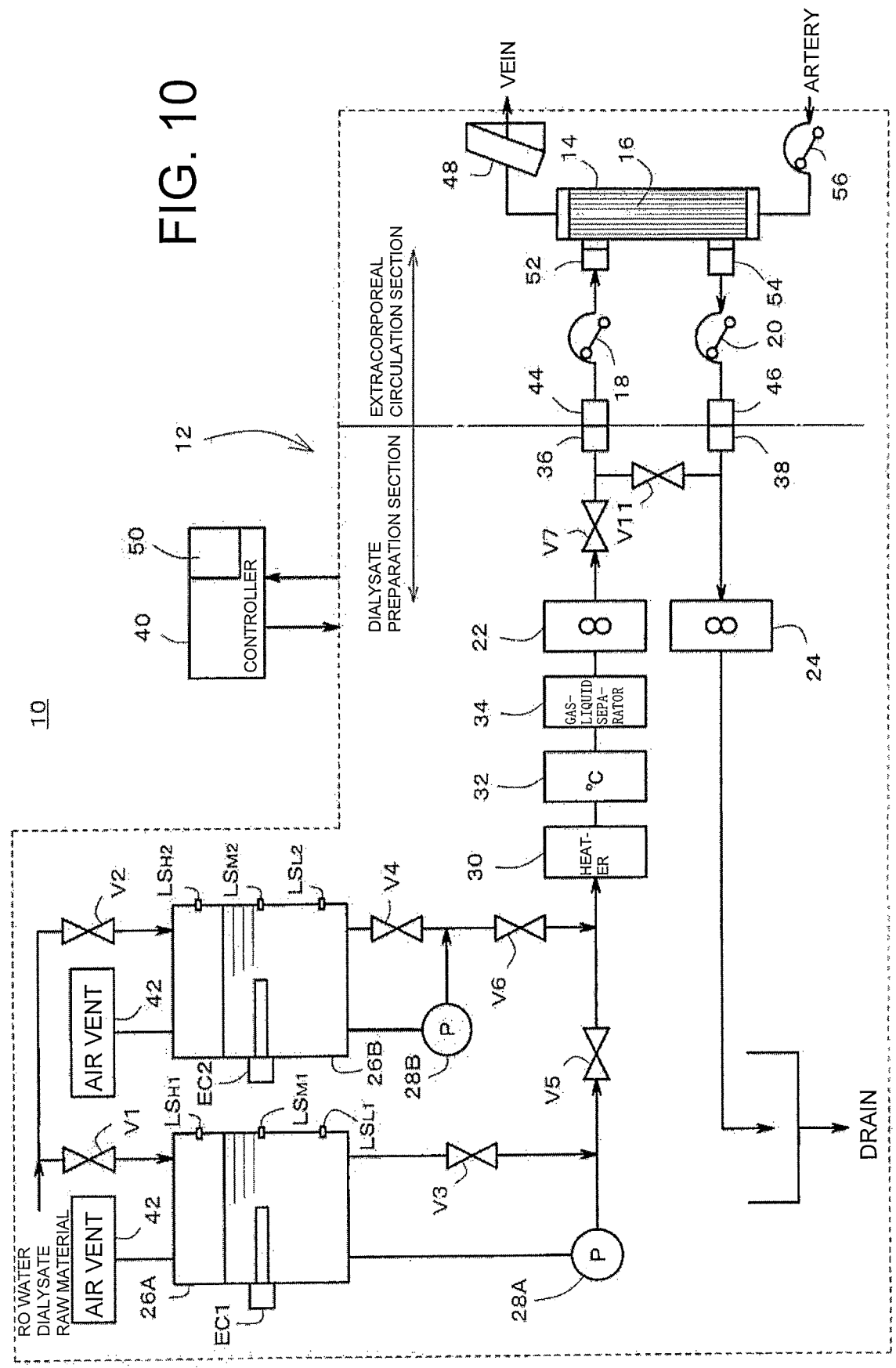
FIG. 10 schematically illustrates another example blood dialysis system according to the present embodiment.

FIG. 8 illustrates an example calibration process (3). During execution of priming, the device-side In coupler 36 and the purifier-side In coupler 44 are coupled with each other, and the device-side Out coupler 38 and the purifier-side Out coupler 46 are coupled with each other, and therefore the flow channel at the time of calibration goes through the liquid feeding pump 18 and the liquid discharging pump 20.

In this calibration process (3), the flow channel of the dialysate is coupled to the blood circuit. Therefore, calibration is performed with the clamp 48 being closed and the tube pump 56 in the blood circuit close to the artery being stopped to block the tube, thereby preventing outflow of the dialysate into the blood circuit.

This calibration process (3) is particularly preferable when the liquid feeding pump 18 and the liquid discharging pump 20 are pumps which do not block the flow channel, such as a centrifugal pump. Further, as the dialysate is heated to a temperature for the dialysis therapy by priming, in the inflow flowmeter 22 and the outflow flowmeter 24 through which the dialysate flows, the expansion coefficient of a member surrounding the measurement chamber of the flowmeter (metal member, for example) is equal to the expansion coefficient of the member obtained when the quantity of fluid removal is obtained. Calibration performed under such an environment enables acquisition of more accurate calibration results.

While, in the examples described above, two tanks, namely the first tank 26A and the second tank 26B, are provided, the structure is not limited to this example. A single tank may be provided or three or more tanks may be provided.

While in the above examples, the liquid having a known volume is obtained using the measurements of the level sensors $LS_{L1}$, $LS_{M1}$, $LS_{H1}$, $LS_{L2}$, $LS_{M2}$, and $LS_{H2}$ disposed in the first and second tanks 26A and 26B, the structure is not limited to this example. When the volumes of the first and second tanks are known, for example, the first and second tanks may be filled with liquid up to the upper limit of the volume of the tanks by allowing the liquid to overflow, thereby obtaining the volume of the liquid. Further, when a weight sensor for measuring the weight of liquid and a container (tank or bag) storing the liquid is provided, the volume of the liquid may be obtained by acquiring the measurements of the weight sensor while the liquid is stored in the container.

Further, while in the above examples, the route as indicated in FIG. 3 is used as a bypass route, the bypass route is not limited to this example. A bypass route may be formed by attaching a bypass coupler 60 to the device-side In coupler 36 and the device-side Out coupler 38, as illustrated in the upper section of FIG. 9, for example.

Further, as illustrated in the center section in FIG. 9, when a valve V8 is disposed between the device-side Out coupler 38 and the outflow flowmeter 24, and a bypass tube 62 which bypasses a channel between the inflow flowmeter 22 and the valve V7 and a channel between the outflow flowmeter 24 and the valve V8 is further disposed, this bypass tube may be used to form a bypass route. Specifically, the valves V7 and V8 are closed and a valve V9 of the bypass tube 62 is opened.

As illustrated in the lower section in FIG. 9, when a bypass tube 64 is disposed in the extracorporeal circulation section, this bypass tube may be used to form a bypass route. The bypass tube 64 is formed by coupling a channel between the purifier-side In coupler 44 and the liquid feeding pump 18 and a channel between the purifier-side Out coupler 46 and the liquid discharging pump 20. When forming the bypass route, the valve V10 of the bypass tube 64 is opened, while a channel between the bypass tube 64 and the liquid feeding pump 18 and a channel between the bypass tube 64 and the liquid discharging pump 20 are blocked by the clamps 48, for example.

Other Embodiments

While in the above embodiment, calibration of the inflow flowmeter 22 and the outflow flowmeter 24 has been described, a so-called self-diagnosis process may be additionally performed. Self-diagnosis refers to a process for passing a prescribed quantity of liquid through both the inflow flowmeter 22 and the outflow flowmeter 24 after calibration and comparing the measurements (integrated values). The existence of a difference between the measurements in spite of the calibration process may indicate some operation malfunction in at least one of the inflow flowmeter 22 and the outflow flowmeter 24. Execution of such self-diagnosis during fluid removal or dialysis process, for example, can provide a simple confirmation in which the inflow flowmeter 22 and the outflow flowmeter 24 are operating normally. When the difference in the measurements between the inflow flowmeter 22 and the outflow flowmeter 24 exceeds a predetermined threshold in the self-diagnosis, a safety operation would be executed by issuing an alarm or by stopping fluid removal or dialysis therapy, thereby securing safety for a patient under treatment.

In the present embodiment, the quantity of flow of the liquid supplied to the inflow flowmeter 22 and the outflow flowmeter 24 in the self-diagnosis process is smaller than that in the calibration process. In integrating flowmeters, in which an error is accumulated during the course of integration, the accuracy for error correction increases as the quantity of flow of liquid increases. In the calibration process, approximately 1 L to 2 L of liquid, for example, is supplied in order to correct the error with high accuracy.

On the contrary, because the self-diagnosis is a simplified determination after the calibration process and the time period during which treatment is interrupted should be minimized, the quantity of flow of the liquid which is passed through the inflow flowmeter 22 and the outflow flowmeter 24 is set to be relatively small. In the self-diagnosis process, about 75 mL of liquid is passed through the inflow flowmeter 22 and the outflow flowmeter 24 and the integrated values of these flowmeters are compared with each other.

FIGS. 10 to 13 illustrate a blood dialysis system 10 capable of execution of the self-diagnosis process during the dialysis therapy process. The illustrated example is characterized by a bypass valve V11 additionally disposed in the blood dialysis system 10 illustrated in FIG. 1. The bypass valve V11 is disposed in a bypass flow channel which diverges from a flow channel between the valve V7 and the device-side In coupler 36 and is connected between the device-side Out coupler 38 and the outflow flowmeter 24.

Figure 11:
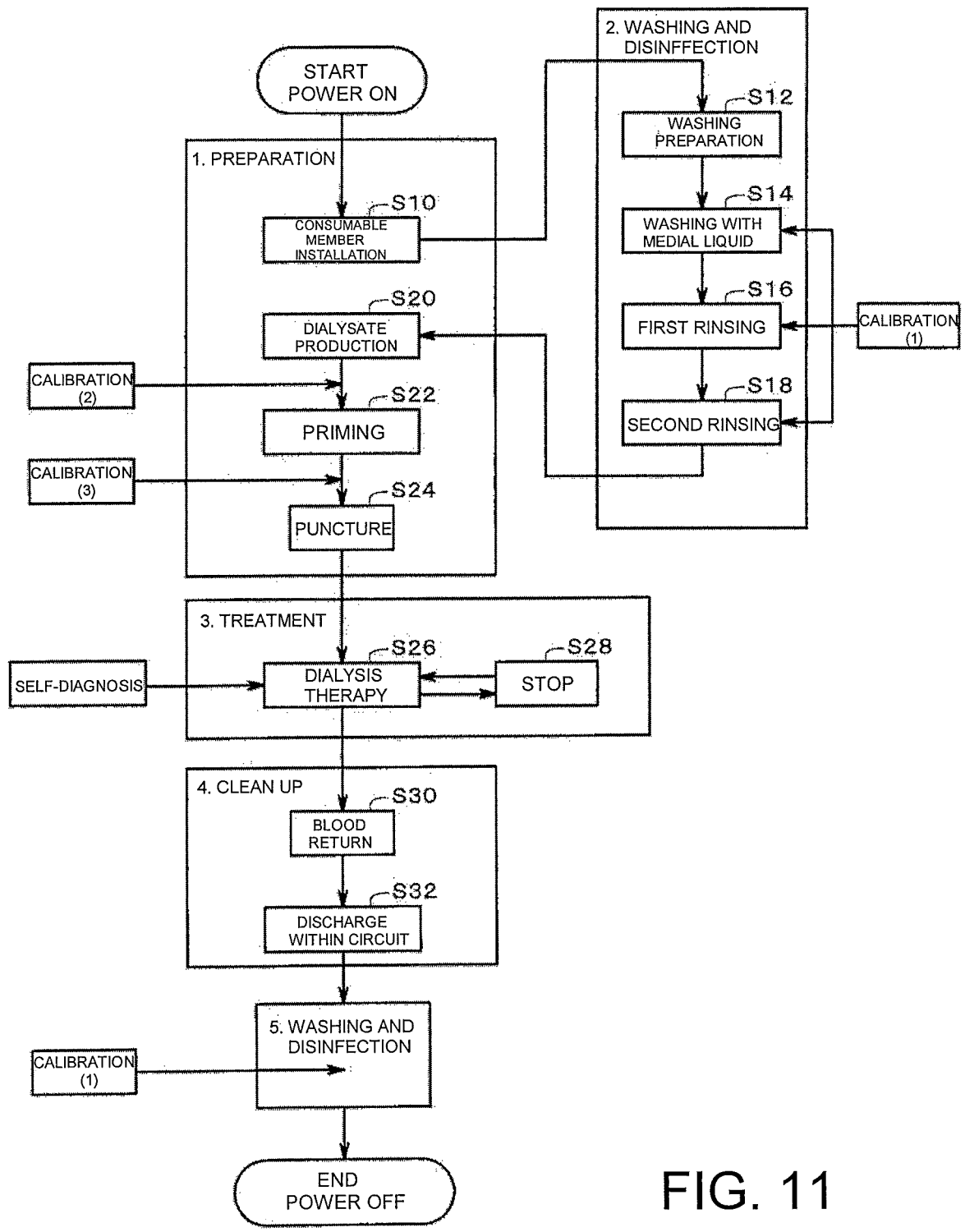
FIG. 11 is a flowchart showing another example blood dialysis flow according to the present embodiment.

FIG. 11 shows a flowchart of a dialysis therapy process in the blood dialysis system according to the present embodiment. This flowchart is characterized in that a self-diagnosis process is inserted during the dialysis therapy in the flowchart shown in FIG. 2.

Figure 12:
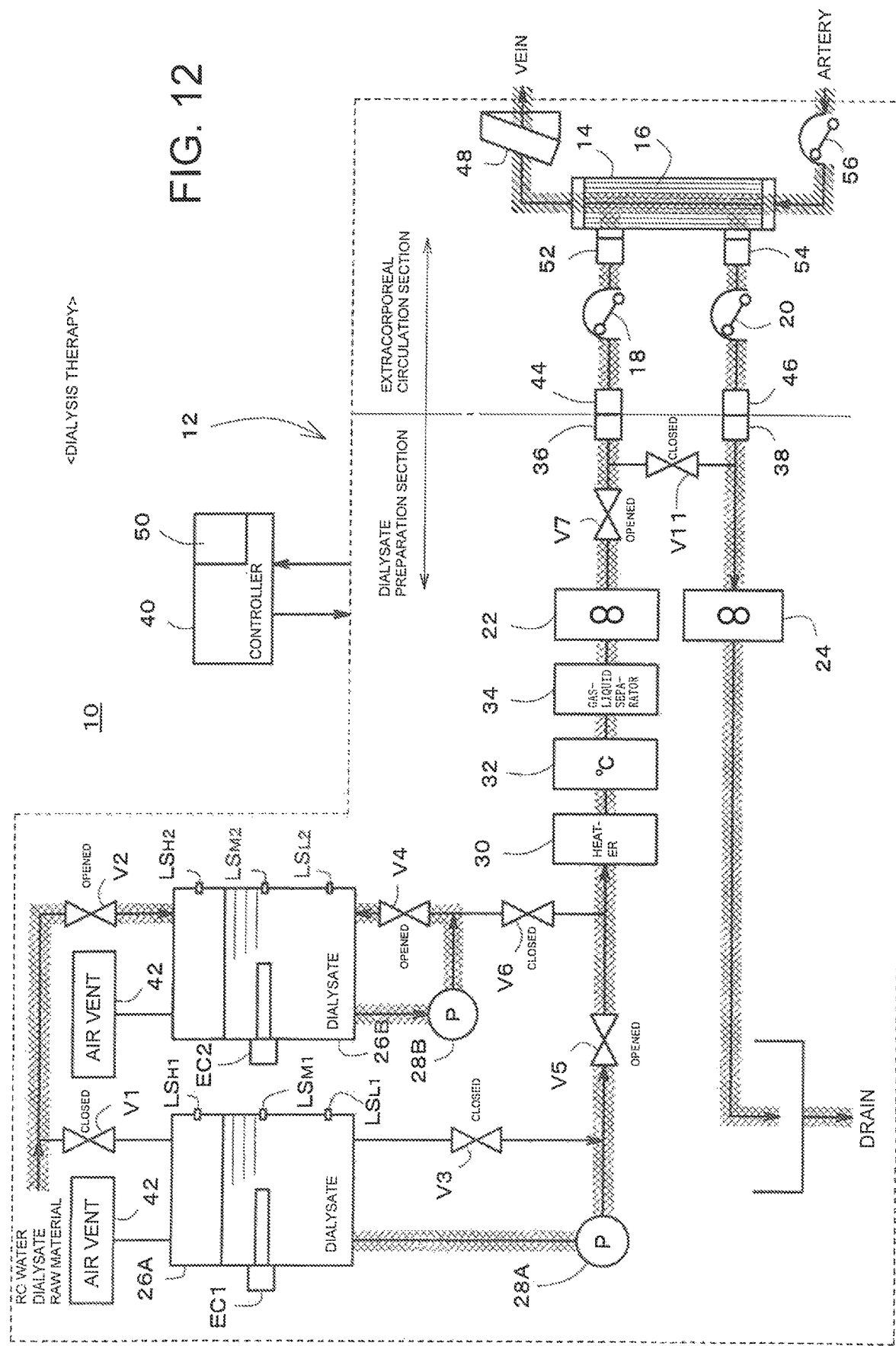
FIG. 12 explains a dialysis therapy process.

More specifically, during the dialysis therapy, the bypass valve V11 is closed, as illustrated in FIG. 12. At this time, as indicated by cross-hatching in FIG. 12, the dialysate is delivered to the blood purifier 14. In the example illustrated in FIG. 12, the dialysate is supplied using the pump 28A, with the valve V3 being closed. Blood is also delivered to the blood purifier 14, as indicated by slanting line hatching in FIG. 12. The dialysate and the blood undergo substance exchange via the hollow fiber membrane 16 which is a dialysis membrane.

Figure 13:
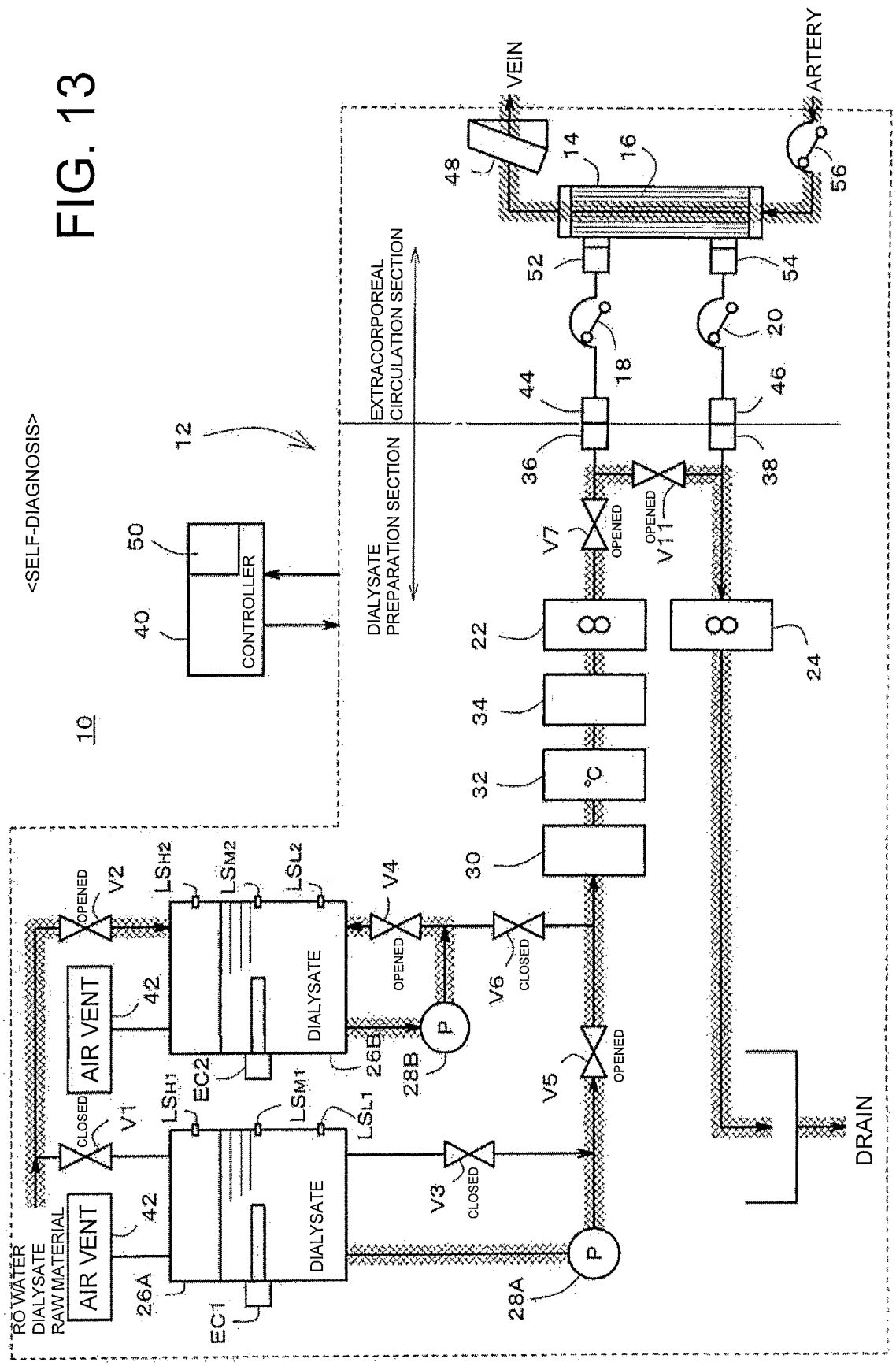
FIG. 13 explains a self-diagnosis process.

FIG. 13 illustrates the self-diagnosis process. The self-diagnosis process is executed during the dialysis therapy. After elapse of a predetermined time (e.g., 1 hour) from the previous self-diagnosis, for example, the self-diagnosis is performed while the dialysis therapy is temporarily stopped.

In the self-diagnosis process, the liquid feeding pump 18 and the liquid discharging pump 20 are stopped, and the bypass valve V11 is opened. When the liquid feeding pump 18 and the liquid discharging pump 20 are tube pumps, cessation of driving of the pumps causes the tube to be blocked, which interrupts supply of the dialysate to the blood purifier 14.

In this state, the dialysate is supplied from the first tank 26A or the second tank 26B. When the dialysate is supplied from the first tank 26A, the dialysate flows through the following route indicated by cross-hatching in FIG. 13: first tank 26A→pump 28A→valve V5→heater 30→temperature sensor 32→gas-liquid separator 34→inflow flowmeter 22→valve V7→bypass valve V11→outflow flowmeter 24→drain.

At this time, the controller 40 monitors the pulse number of the inflow flowmeter 22 and the outflow flowmeter 24. The controller 40 refers to the pulse number of the outflow flowmeter 24 obtained when the pulse number of the inflow flowmeter 22 reaches 300 pulses, for example. When the quantity of flow corresponding to 1 pulse is 0.25 mL, for example, the quantity of flow of dialysate corresponding to 300 pulses would be only 75 mL.

The controller 40 compares the pulse numbers between the inflow flowmeter 22 and the outflow flowmeter 24 and obtains the difference between the pulse numbers. When the pulse number of the outflow flowmeter 24 is within the range of 300±2, the controller 40 determines that the outflow flowmeter 24 is normal. The controller 40 thereafter closes the bypass valve V11 and actuates the liquid feeding pump 18 and the liquid discharging pump 20, thereby resuming the dialysis therapy.

When the pulse number of the outflow flowmeter 24 is above 300+2 or below 300−2, the controller 40 determines that the outflow flowmeter 24 is abnormal. Upon determination of abnormality, the controller 40 stops the dialysis therapy and issues an alarm, for example, thereby securing safety for the patient.

During the dialysis therapy, calcium carbonate and magnesium, for example, in the dialysate may be deposited on the outflow flowmeter 24, causing deviation in the measurements, for example. Execution of the self-diagnosis during the dialysis therapy as described above would secure accuracy in measurements of the outflow flowmeter 24 during the dialysis therapy.

When an abnormality determination is made during the self-diagnosis, there is a possibility that the inflow flowmeter 22, not the outflow flowmeter 24, is abnormal. Therefore, the controller 40 may output a message that at least one of the inflow flowmeter 22 and the outflow flowmeter 24 is abnormal, as the content of the abnormality determination.

During the execution period of the self-diagnosis process, the extracorporeal circulation system is preferably not stopped in order to prevent coagulation of blood. For example, during the execution period of the self-diagnosis process, the blood pump 56 is placed in a driven state. When the self-diagnosis process is to be terminated in a short time, the blood pump 56 may be stopped to thereby temporarily stop the extracorporeal circulation system.

In place of or in addition to execution of the self-diagnosis during the dialysis therapy, the calibration process may be executed. While the calibration process requires a higher quantity of flow of the dialysate than that in the self-diagnosis, calibration may be performed during the dialysis therapy when it is necessary to obtain the difference in measurements between the inflow flowmeter 22 and the outflow flowmeter 24 with high accuracy (e.g., when the pulse number of the outflow flowmeter 24 was 302 in the previous self-diagnosis).

When the result of the previous calibration process can be used as it is in the following calibration process, such as when, upon completion of a series of blood dialysis flow illustrated in FIG. 11, the following blood dialysis flow is executed immediately after that, for example, calibration (1) to (3) shown in FIG. 11 may be replaced with self-diagnosis. Such replacement reduces the quantity of the dialysate to be consumed and shortens the time required for the blood dialysis flow.

REFERENCE SIGNS LIST 10 blood dialysis system, 12 blood dialyzer, 14 blood purifier, 16 hollow fiber membrane, 18 liquid feeding pump, 20 liquid discharging pump, 22 inflow flowmeter, 24 outflow flowmeter, 26A first tank, 26B second tank, 28A, 28B stirring pump, 30 heater, 32 temperature sensor, 34 gas-liquid separator, 36 device-side In coupler, 38 device-side Out coupler, 40 controller, 44 purifier-side In coupler, 46 purifier-side Out coupler, 50 computing unit, 52 dialysate In coupler, 54 dialysate Out coupler, 56 blood pump.

The invention claimed is:
1. A calibration method for flowmeters in a blood dialysis system, the blood dialysis system comprising:
   a blood purifier comprising a dialysis membrane, dialysate and blood being supplied to the blood purifier to undergo substance exchange therebetween, via the dialysis membrane;
   a liquid feeding pump configured to supply the dialysate to the blood purifier;
   a liquid discharging pump configured to discharge the dialysate from the blood purifier;
   an inflow flowmeter configured to measure a quantity of flow of the dialysate to be supplied to the blood purifier;
   an outflow flowmeter configured to measure a quantity of flow of the dialysate to be discharged from the blood purifier; and
   a calculation unit configured to measure a quantity of fluid removal from the blood based on a difference in measurements between the inflow flowmeter and the outflow flowmeter,
   the calibration method comprising:
   supplying liquid to a flow channel passing through the inflow flowmeter and the outflow flowmeter while preventing outflow of the liquid to a blood flow channel in the blood purifier; and
   performing correction to match the measurements of the outflow flowmeter obtained when the liquid is supplied with the measurements of the inflow flowmeter, thereby calibrating the inflow flowmeter and the outflow flowmeter.

2. The calibration method for flowmeters in a blood dialysis system according to claim 1, wherein
   after the calibration of the inflow flowmeter and the outflow flowmeter, liquid having a quantity of flow which is smaller than a quantity of flow of liquid supplied to the inflow flowmeter and the outflow flowmeter during the calibration is supplied to the flow channel passing through the inflow flowmeter and the outflow flowmeter while preventing outflow of the liquid to a blood flow channel in the blood purifier; and
   based on a difference between the measurements of the outflow flowmeter and the measurements of the inflow flowmeter obtained when the liquid is supplied, self-diagnosis for determining presence of operation abnormality in the inflow flowmeter and the outflow flowmeter is performed.

3. The calibration method for flowmeters in a blood dialysis system according to claim 2, wherein
   the self-diagnosis is executed during dialysis therapy.

4. The calibration method for flowmeters in a blood dialysis system according to claim 2, wherein
   the blood dialysis system further comprises a blood pump configured to supply blood to the blood purifier, and
   during the self-diagnosis, the blood pump is in a driven state.

5. The calibration method for flowmeters in a blood dialysis system according to claim 2, wherein
   when blood dialysis is executed after the calibration of the inflow flowmeter and the outflow flowmeter and immediately after completion of this blood dialysis, further blood dialysis is performed, the self-diagnosis is executed, in place of the calibration, during the further blood dialysis.

6. The calibration method for flowmeters in a blood dialysis system according to claim 1, wherein the preventing outflow of the liquid to the blood flow channel in the blood purifier includes
   disconnecting a first channel between the inflow flowmeter and the liquid feeding pump, disconnecting a second channel between the outflow flowmeter and the liquid discharging pump, and forming a bypass route that connects the inflow flowmeter and the outflow flowmeter.

7. A calibration method for flowmeters in a blood dialysis system, the blood dialysis system comprising:

a blood purifier comprising a dialysis membrane, dialysate and blood being supplied to the blood purifier to undergo substance exchange therebetween via the dialysis membrane;

a liquid feeding pump configured to supply the dialysate to the blood purifier;

a liquid discharging pump configured to discharge the dialysate from the blood purifier;

an inflow flowmeter configured to measure a quantity of flow of the dialysate to be supplied to the blood purifier;

an outflow flowmeter configured to measure a quantity of flow of the dialysate to be discharged from the blood purifier; and a calculation unit configured to measure a quantity of fluid removal from the blood based on a difference in measurements between the inflow flowmeter and the outflow flowmeter, the calibration method comprising:

supplying an entire quantity of liquid having a known volume to a flow channel passing through the inflow flowmeter and the outflow flowmeter while preventing outflow of the liquid to a blood flow channel in the blood purifier; and calibrating the measurements of the inflow flowmeter and the outflow flowmeter based on the known volume.

8. The calibration method for flowmeters in a blood dialysis system according to claim 7, wherein the calibration is performed when a bypass route that bypasses the liquid feeding pump and the liquid discharging pump is formed.

9. The calibration method for flowmeters in a blood dialysis system according to claim 7, wherein a tank connected upstream of the flow channel passing through the inflow flowmeter and the outflow flowmeter is disposed relatively upward in an normal direction among elements forming the blood dialysis system, and during the calibration, liquid is supplied from the tank through gravity feed.

10. The calibration method for flowmeters in a blood dialysis system according to claim 9, wherein the tank is a tank connected upstream of the flow channel passing through the inflow flowmeter and the outflow flowmeter, is the tank being configured to store dialysate.

11. The calibration method for flowmeters in a blood dialysis system according to claim 7, wherein the blood dialysis system further comprises stirring pump configured to mix a raw material of the dialysate and a solvent, and during the calibration, liquid is supplied by the stirring pump.

12. The calibration method for flowmeters in a blood dialysis system according to claim 7, wherein the liquid having a known volume is obtained by filling a tank having a known volume with the liquid to an upper limit of the volume.

13. The calibration method for flowmeters in a blood dialysis system according to claim 7, wherein the liquid having a known volume is obtained by storing the liquid in a tank including a liquid level sensor and acquiring measurements of the liquid level sensor.

14. The calibration method for flowmeters in a blood dialysis system according to claim 7, wherein the liquid having a known volume is obtained by storing the liquid in a container including a weight sensor and acquiring measurements of the weight sensor.

15. The calibration method for flowmeters in a blood dialysis system according to claim 7, wherein the inflow flowmeter and the outflow flowmeter are calibrated during a final rinsing process in a washing process of supplying washing liquid to the flow channel passing through the inflow flowmeter and the outflow flowmeter and rinsing the washing liquid.

16. The calibration method for flowmeters in a blood dialysis system according to claim 7, wherein the preventing outflow of the liquid to the blood flow channel in the blood purifier includes disconnecting a first channel between the inflow flowmeter and the liquid feeding pump, disconnecting a second channel between the outflow flowmeter and the liquid discharging pump, and forming a bypass route that connects the inflow flowmeter and the outflow flowmeter.

* * * * *